United States Patent
Kurdyumov et al.

(10) Patent No.: US 9,487,663 B2
(45) Date of Patent: *Nov. 8, 2016

(54) PHOTOACTIVATABLE CROSSLINKER

(71) Applicant: SurModics, Inc., Eden Prairie, MN (US)

(72) Inventors: Aleksey V. Kurdyumov, Maplewood, MN (US); Dale G. Swan, St. Louis Park, MN (US)

(73) Assignee: Surmodics, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/541,768

(22) Filed: Nov. 14, 2014

(65) Prior Publication Data

US 2015/0166801 A1 Jun. 18, 2015

Related U.S. Application Data

(63) Continuation of application No. 13/074,537, filed on Mar. 29, 2011, now Pat. No. 8,889,760.

(60) Provisional application No. 61/319,127, filed on Mar. 30, 2010.

(51) Int. Cl.
*C07F 9/145* (2006.01)
*C09D 7/12* (2006.01)
(Continued)

(52) U.S. Cl.
CPC .......... *C09D 7/1233* (2013.01); *A61L 17/145* (2013.01); *A61L 27/34* (2013.01);
(Continued)

(58) Field of Classification Search
CPC ................................................ C07F 9/4025
See application file for complete search history.

(56) References Cited

U.S. PATENT DOCUMENTS 3,352,896 A    11/1967   Dressler et al.
3,395,116 A *   7/1968   Dressler et al. .............. 524/265
(Continued)

FOREIGN PATENT DOCUMENTS

EP   1557413   7/2005
EP   2552927   2/2013
(Continued)

OTHER PUBLICATIONS

Chekmacheva et al. Phosphorylated derivatives of hydroxybenzophenones. I. Synthesis and properties of phosphorylated derivatives of p-hydroxybenzophenone Zhurnal Obshchei Khimii (1983), 53(2), 243-247; Plenum Publishing Corporation.*

(Continued)

*Primary Examiner* — Michael Pepitone
(74) *Attorney, Agent, or Firm* — Pauly, Devries Smith & Deffner, L.L.C.

(57) ABSTRACT

Described herein is a degradable linking agent of formula Photo$^1$-LG-Photo$^2$, wherein Photo$^1$ and Photo$^2$ independently represent at least one photoreactive group and LG represents a linking group comprising one or more silicon atoms or one or more phosphorous atoms. The degradable linking agent includes a covalent linkage between at least one photoreactive group and the linking group, wherein the covalent linkage between at least one photoreactive group and the linking group is interrupted by at least one heteroatom. A method for coating a support surface with the degradable linking agent, coated support surfaces and medical devices are also described.

12 Claims, 3 Drawing Sheets

(51) Int. Cl.

| | |
|---|---|
| A61L 17/14 | (2006.01) |
| A61L 27/34 | (2006.01) |
| A61L 29/08 | (2006.01) |
| A61L 31/10 | (2006.01) |
| C07F 7/10 | (2006.01) |
| C07F 7/18 | (2006.01) |
| C07F 9/12 | (2006.01) |
| C07F 9/40 | (2006.01) |
| C08F 2/48 | (2006.01) |
| C07F 9/06 | (2006.01) |
| C08K 5/51 | (2006.01) |
| C08K 5/5419 | (2006.01) |
| C08K 5/544 | (2006.01) |

(52) U.S. Cl.
CPC ............ A61L 29/085 (2013.01); A61L 31/10 (2013.01); C07F 7/10 (2013.01); C07F 7/184 (2013.01); C07F 7/1804 (2013.01); C07F 9/06 (2013.01); C07F 9/12 (2013.01); C07F 9/145 (2013.01); C07F 9/4025 (2013.01); C07F 9/4084 (2013.01); C08F 2/48 (2013.01); C08K 5/51 (2013.01); C08K 5/544 (2013.01); C08K 5/5419 (2013.01); A61L 2400/18 (2013.01); A61L 2420/02 (2013.01)

(56) References Cited

U.S. PATENT DOCUMENTS

| | | | |
|---|---|---|---|
| 3,869,527 A * | 3/1975 | Hogberg et al. | 558/198 |
| 4,954,534 A | 9/1990 | Yamamuro | |
| 5,002,582 A | 3/1991 | Guire et al. | |
| 5,069,719 A * | 12/1991 | Ono | 524/130 |
| 5,942,555 A * | 8/1999 | Swanson et al. | 522/35 |
| 6,077,698 A | 6/2000 | Swan et al. | |
| 7,087,658 B2 | 8/2006 | Swan et al. | |
| 7,176,297 B2 | 2/2007 | Li et al. | |
| 7,244,444 B2 | 7/2007 | Bates | |
| 8,668,667 B2 * | 3/2014 | Chappa | 604/101.02 |
| 8,889,760 B2 | 11/2014 | Kurdyumov et al. | |
| 2011/0245367 A1 | 10/2011 | Kurdyumov et al. | |
| 2012/0046384 A2 | 2/2012 | Kurdyumov et al. | |
| 2012/0149934 A1 | 6/2012 | Kurdyumov | |

FOREIGN PATENT DOCUMENTS

| | | |
|---|---|---|
| GB | 1406611 | 9/1975 |
| JP | S45030568 | 10/1970 |
| JP | 6429384 | 1/1989 |
| JP | H02187437 | 7/1990 |
| JP | 2002138283 | 5/2002 |
| JP | 2007264291 | 10/2007 |
| MX | 339181 | 5/2016 |
| WO | 0248204 | 6/2002 |
| WO | 2007003507 | 1/2007 |
| WO | 2011072199 | 6/2011 |
| WO | 2011123441 | 10/2011 |

OTHER PUBLICATIONS

Andrianov, K. A. et al., "Some Diketodicarboxylic Silicoorganic Acids," Journal of General Chemistry of the USSR, vol. 31, No. 1, (1961), pp. 218-221.
Andrianov, K. A. et al., "Acylation of Arylaliphatic Disiloxanes," Journal of General Chemistry of the USSR, vol. 29, (1959), pp. 2669-2672.
Braun, D. I. "Plastics," Concise Encyclopedia of Polymer Science and Engineering, (1990), pp. 462-464.
Chekmacheva, O. I. et al., "Phosphorylated Derivatives of Hydroxybenzophenones. I. Synthesis and Properties of Phosphorylated Derivatives of p-hydroxybenzophenone," Journal of General Chemistry of the USSR, vol. 53, No. 2, (1983), pp. 243-247.
Chekmacheva, O. I. et al., "Phosphorylated Hydroxybenzophenones. II. Synthesis and Properties of Phosphorylated o-hydroxybenzophenones," Journal of General Chemistry of the USSR, vol. 53, No. 4, (1983), pp. 653-655.
"Communication Pursuant to Article 94(3) EPC," for European Patent Application No. 11713146.6 mailed on Jul. 2, 2015 (4 pages).
"Communication Pursuant to Article 94(3) EPC," for European Patent Application No. 11713146.6, mailed Jul. 7, 2014 (4 pages).
"Communication Pursuant to Rules 161(1) and 162 EPC," for European Patent Application No. 11713146.6, mailed Nov. 9, 2012 (2 pages).
"Final Office Action," for U.S. Appl. No. 13/074,537, mailed Aug. 20, 2014 (10 pages).
"Final Office Action," for U.S. Appl. No. 13/316,030, mailed Aug. 14, 2014 (18 pages).
"First Office Action," for Chinese Patent Application No. 201180021034.3, mailed Jun. 5, 2014, 21 pages with English translation.
George, Maurice H. et al., "The Synthesis of Precisely Structured Polyurethanes. Part 2. Chain Building Methodology," Journal of the Chemical Society, Perkin Transacti ons 1, No. 12, (1996), pp. 1395-1401.
Harper, S. D. et al., "Intramolecular Oxidative Cyclization Reactions of Trivalent Phosphorus and Carbonyl Functions," Journal of the American Chemical Society, vol. 104, No. 9, (1982), pp. 2497-2501.
Ismail, Roshdy M. et al., "Uber die Herstellung and UV-Absorption einiger Siliciumester and Metalle enthaltender Benzophenon-Derivate," Zeitschrift Fuer Naturforschung, Teil B: Anorganische Chemie, Organische Chemie, vol. 25, (1970), pp. 14-18.
"Non-Final Office Action," for Russian Patent Application No. 2012144225, mailed May 18, 2015 (6 pages) with English translation.
"Non-Final Office Action," for Japanese Patent Application No. 2013-502749, mailed Jan. 27, 2015 (8 pages) with English translation.
"Non-Final Office Action," for U.S. Appl. No. 13/074,537, mailed May 22, 2014 (20 pages).
"Non-Final Office Action," for U.S. Appl. No. 13/316,030, mailed Dec. 24, 2013 (6 pages).
"Non-Final Office Action," for U.S. Appl. No. 13/316,030, mailed Jun. 29, 2015 (20 pages).
"Notice of Allowance," For U.S. Appl. No. 13/074,537, mailed Oct. 7, 2014 (15 pages).
"Nucleophilic Substitution—SN1—Elimination," http://chemistry2.csudh.edu/rpendarvis/SN1Elim.html, 2001, pp. 1-7.
"Nucleophilic Substitution—SN2," http://chemistry2.csudh.edu/rpendarvis/SN2.html, 2001, pp. 1-6.
"Office Action Received," for Russian Application No. 2012144225, mailed Dec 19, 2012 (3 pages).
"Office Action," for Mexico Patent Application No. MX/a/2012/011061, mailed Aug. 10, 2014 (1 page).
"Office Action," for Mexico Patent Application No. MX/a/2012/011061, mailed May 7, 2015 (3 pages).
"Office Action," for Russian Patent Application No. 2012144225, mailed Jan. 27, 2015 (8 pages) with English Translation.
"PCT International Search Report and Written Opinion," from International Application No. PCT/US2011/030319, corresponding to U.S. Appl. No. 61/422,333, mailed Jul. 22, 2011, (15 pages).
"PCT Inernational Preliminary Report," from International Application No. PCT/US2011/030319, mailed Oct. 11, 2012, (8 pages).
Pinkus, A. G. et al., "Reactions of Chlorosilanes and 5-chloro-2-hydroxybenzophenone," The Journal of Organic Chemistry, vol. 34, No. 4, (1969), pp. 1094-1097.
"Response to Communication Pursuant to Article 94(3) EPC," for European Patent Application No. 11713146.6, mailed Jul. 7, 2014 and filed with the EPO Dec. 30, 2014 (14 pages).
"Response to Communication Pursuant to Rules 161(1) and 162 EPC," for European Patent Application No. 11713146.6, mailed Nov. 9, 2012 and filed with the EPO Apr. 5, 2013 (12 pages).

(56) References Cited

OTHER PUBLICATIONS

"Response to Final Office Action," for U.S. Appl. No. 13/074,537, mailed Aug. 20, 2014 and filed with the USPTO Sep. 18, 2014 (5 pages).
"Response to Final Office Action," for U.S. Appl. No. 13/316,030, mailed Aug. 14, 2014 and filed with the USPTO Jan. 14, 2015 (6 pages).
"Response to Non-Final Office Action," for U.S. Appl. No. 13/074,537, mailed May 22, 2014 and filed with the USPTO Jul. 16, 2014 (7 pages).
"Response to Non-Final Office Action," for U.S. Appl. No. 13/316,030, mailed Dec. 24, 2013 and filed with the USPTO Apr. 24, 2014 (3 pages).
"Second Office Action," for China Patent Application No. 201180021034.3, mailed Mar. 26, 2015 (15 pages) including English translation.
Segal, John A. "Aromatic Polyether Synthesis via Activated in a Ruthenium(II) Complex of p-dichlorobenzene," Journal of the Chemical Society, Chemical Communications, No. 19, (1985), pp. 1338-1339.
"Selected Aspects of Organosilicon Chemistry," Chapter 9, (2006), pp. 1-5.
"Silane Chemistry Primer," Dow Corning, (1995), pp. 1-4.
Singh, M. S. et al., "Synthesis and Spectroscopic studies of 2-(N-salicylidene)-5-chlorobenzophenone Derivatives of Organosilicon(IV)," Phosphorus, Sulfur and Silicon and the Related Elements, vol. 130, (1997), pp. 147-153.
Wiese, Dietmar et al., "1,3-Bis(2-benzoylphenyl)-1,1,3,3-Tetramethyldisiloxan," Chemische Berichte,vol. 120, No. 6, (1987), pp. 873-878.
"CAS RN 41351-06-8," Nov. 16, 1984.
"CAS RN 41351-07-9," Nov. 16, 1984.
"CAS RN 41351-26-2," Nov. 16, 1984.
"CAS RN 730911-91-8," Aug. 22, 2004.
"CAS RN 767584-93-0," Oct. 22, 2004.
"CAS RN 780693-90-5," Nov. 14, 2004.
"CAS RN 86967-57-9," Nov. 16, 1984.

Chekmacheva, O.I. et al., "Phosphorylated Derivatives of Hydroxybenzophenones," Zhurnal Obshchei Hkimii, 1983, 53(5), pp. 1028-1031.
Non-Final Office Action, for Russian Patent Application No. 2012144225, mailed Oct. 19, 2015 (6 pages) with English translation.
Non-Final Office Action, for U.S. Appl. No. 13/316,030 mailed Jan. 12, 2016 (10 pages).
Office Action, for Japanese Patent Application No. 2013-502749, mailed Jan. 5, 2016 (8 pages) with translation.
Response Non-Final Office Action, for U.S. Appl. No. 13/316,030, mailed Jun. 29, 2015 and filed with the USPTO Sep. 28, 2015 (6 pages).
Response to Communication Pursuant to Article 94(3) EPC, for European Patent Application No. 11713146.6, mailed Jul. 2, 2015 and filed with the EPO Dec. 24, 2015 (13 pages).
Schilling, Jansen H. et al., "Syntheses of Styrene and Butadien Cyclosiloxan Block Copolymer Having UV Absorber Residues," Acta Polymerica, 1989, 40(2), pp. 116-121.
Third Office Action, for Chinese Patent Application No. 201180021034.3, mailed Dec. 15, 2015 (20 pages) including English translation.
Third Office Action, for Mexican Patent Application No. MX/a/2012/011061, mailed Nov. 8, 2015 (1 page).
Vysokomolekulyarnye Soedineniya, 1959, 1, pp. 704-710.
Wiese, Dietmar et al., "1,3-Bis(2-benzoylphenyl)-1,1,3,3-tetramethyldisiloxan," Chemische Berichte, 1987, 120(6), pp. 873-878.
Zhurnal Obshchei Khimii, 1959, 20, pp. 2702-2706.
Response to Non-Final Office Action, for U.S. Appl. No. 13/316,030, mailed Jan. 12, 2016 and filed with the USPTO May 12, 2016 (5 pages).
Decision of Rejection, for Japanese patent application No. 2013-502749 mailed Aug. 30, 2016 (7 pages) with English Translation.
Fourth Office Action, for Chinese Patent Application No. 201180021034.3 mailed Sep. 6, 2016 (10 pages) with English Translation.

* cited by examiner

Where X = O, CH$_2$, and OCH$_2$CH$_2$O
O(CH$_2$CH$_2$O)$_n$

Where M = Li, Na, and K

Where BP is benzophenone
R is benzophenone or alkyl 4-hydroxybenzophenone

Where BP is benzophenone
R is alkyl or other chain

PHOTOACTIVATABLE CROSSLINKER

CROSS-REFERENCE TO RELATED APPLICATIONS

This application is a continuation application of U.S. Pat. No. 8,889,760, filed Mar. 29, 2011, which claims the benefit of U.S. Provisional Application No. 61/319,127, filed Mar. 30, 2010, the contents of which are herein incorporated by reference.

TECHNICAL FIELD

The present invention relates to a linking agent having one or more photoactivatable groups. In particular, the invention provides a degradable linking agent.

BACKGROUND OF THE INVENTION

Photochemically reactive functional groups ("photoreactive groups") are functional groups that, when exposed to an appropriate energy source, undergo a transformation from an inactive state (i.e., ground state) to a reactive intermediate capable of forming covalent bonds with appropriate materials. Photoreactive groups can be used, for instance, to derivatize a target molecule (e.g., thermochemically), in order to then photochemically attach the derivatized target molecule to a surface. Photoreactive groups can also be used as photoinitiators for polymerization reactions.

SUMMARY OF THE INVENTION

Disclosed herein is a degradable linking agent having formula Photo$^1$-LG-Photo$^2$, wherein Photo$^1$ and Photo$^2$, independently, represent at least one photoreactive group and LG represents a linking group. In one embodiment, one or more photoreactive groups include an aryl ketone. In a more particular embodiment, one or more photoreactive groups include benzophenone.

In one embodiment, the linking group includes one or more silicon atoms or one or more phosphorus atoms, wherein each photoreactive group is independently bound to the linking group by a covalent linkage that includes at least one heteroatom. In one embodiment, at least one heteroatom is selected from oxygen, nitrogen, selenium, sulfur, or a combination thereof. In one embodiment, at least one photoreactive group, heteroatom and linking group form an ether or an amine.

In a more particular embodiment, the linking group includes one silicon atom covalently bound to at least two photoreactive groups. In another embodiment, the linking group includes at least two silicon atoms. In another embodiment, the linking group has the formula Si—Y—Si, wherein Y represents a linker that can be null, an amine, ether, linear or branched $C_1$-$C_{10}$ alkyl, or a combination thereof. In one embodiment, Y is selected from O, $CH_2$, $OCH_2CH_2O$ and $O(CH_2CH_2O)_n$, wherein n is an integer between 1 and 5, between 1 and 10, between 1 and 15, between 1 and 20, between 1 and 25, or between 1 and 30.

In another embodiment, the linking group includes one or more phosphorester bonds and/or one or more phosphoramide bonds wherein one or more phosphorester and/or one or more phosphoramide bonds form a covalent bond with at least one photoreactive group, such that the linking group includes at least two photoreactive groups. In one embodiment, the linking group is covalently attached to three photoreactive groups, wherein each photoreactive group is covalently bound to the linking group by a phosphorester or phosphoramide bond. In another embodiment, the linking group includes at least one phosphorus atom with a phosphorus-oxygen double bond (P═O), wherein at least one photoreactive group is bound to at least one phosphorus atom. In yet another embodiment, the linking group includes one phosphorus atom with a phosphorus-oxygen double bond (P═O), wherein at least two or three photoreactive groups are covalently bound to the phosphorus atom. In another embodiment, the linking group includes at least two phosphorus atoms, wherein at least one phosphorus atom includes a phosphorus-oxygen double bond (P═O), and at least one or at least two photoreactive groups are covalently bound to each phosphorus atom.

According to one embodiment, the degradable linking agent is capable of, upon activation of one or more photoreactive groups, covalent attachment to a surface, target molecule, or a combination thereof. Also provided is a method of coating a support surface with a linking agent in order to provide the surface with latent reactive groups. In one embodiment, the method includes steps of: providing a support surface; applying to the support surface the degradable linking agent; and illuminating the linking agent upon the support surface under conditions suitable to activate a first photoreactive group to attach the linking agent to the surface, wherein a second photoreactive species remains unbound to the support surface and is able to revert to a latent reactive state. A support surface bearing a coating that includes a polymer layer attached to the surface by a degradable linking agent is also provided, in which a first photoreactive group of the linking agent, when activated in the presence of the support surface, is able to attach the linking agent to the support surface, and a second photoreactive group of the linking agent, when activated in the presence of a coating agent, is able to attach the coating the surface. Also described herein is a combination that includes a medical device and a polymeric coating, wherein the coating is attached to the medical device by a degradable linking agent.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

Figure 1:
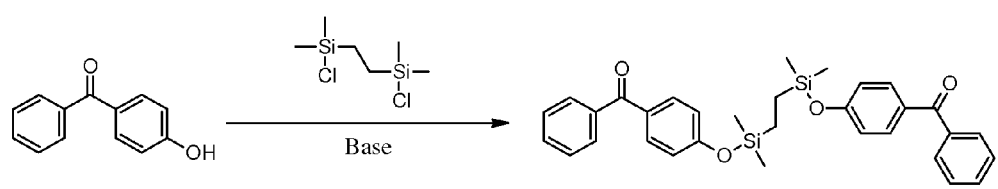
FIG. 1 shows a reaction pathway for the generation of a degradable linking agent as described herein.

While the invention is susceptible to various modifications and alternative forms, specifics thereof have been shown by way of example and drawings, and will be described in detail. It should be understood, however, that the invention is not limited to the particular embodiments described. On the contrary, the intention is to cover all modifications, equivalents, and alternatives falling within the spirit and scope of the invention.

DETAILED DESCRIPTION

Described herein is a degradable linking agent. The degradable linking agent includes one or more photoreactive groups and a linking group, wherein each photoreactive group is independently attached to the linking group by a degradable linkage. In other embodiments, the degradable linking agent includes two or more photoreactive groups. In still other embodiments, the degradable linking agent includes three or more photoreactive groups. In one embodiment, the linking agent is capable of, upon activation of one or more photoreactive groups, covalent attachment to a surface, target molecule, or a combination thereof. In particular, each photoreactive group of the linking agent may be capable of being activated to form a covalent bond with the surface or target molecule.

The linking agent described herein is particularly useful for applications in which it is desirable to have a linking agent that can degrade over time. For example, in some instances, it may be desirable to have a surface coating on an implanted device with one property initially and a different property over time. In such a case, the degradable linking agent can be use to apply a coating on the implanted device that degrades over time to expose a surface or base coat with one or more different properties. In one embodiment, the linking agent is used to attach a hydrophobic coating to a surface. In another embodiment, the linking agent is used to attach a hydrophilic coating to a surface. In yet another embodiment, the degradable linking agent is used to apply a hydrophilic coating on an implantable medical device that will degrade over time to expose a hydrophobic surface or base coat, or vice versa.

In some instances, it may be desirable to include one or more bioactive agents in a surface coating. In one embodiment, the linking agent can be used for delivery of one or more bioactive agents. For example, the linking agent may be suitable for use in combination with a drug delivery coating, in particular for use in connection with bioactive agents that can tolerate (e.g., remain effective) exposure to ultra-violet radiation.

In one embodiment, one or more photoreactive groups of the linking agent can be used as an initiator for photopolymerization. In one embodiment, the linking agent is used in connection with a composition that is capable of in situ polymerization. In one embodiment, the linking agent can be used in connection with a biocompatible, biodegradable polymer foam. In one embodiment, the linking agent is used in connection with a biodegradable foam used for the treatment of wounds, such as deep or cavernous wounds. For example, the linking agent can be used in connection with a biocompatible foam formed using biocompatible monomers or macromers in combination with a polymerization initiator and gas generation components.

In another embodiment, the linking agent can be used in the generation of degradable grafts for tissue engineering. For example, the linking agent can be used to generate a degradable three dimensional structure, sometimes referred to as a polymeric scaffolding or extracellular matrix, for cell attachment and migration. The polymeric scaffolding can be used in connection with tissue engineering technology for the repair and/or replacement of portions of or entire tissues and/or organs (e.g., bone, cartilage, blood vessels, bladder, etc.). In addition to providing a scaffolding with a desired porosity and pore size to facilitate cell seeding and diffusion of both cells and nutrients, the linking agent is biodegradable. Biodegradability is often an important factor in the development of tissue scaffolding, so that the graft can be absorbed by the surrounding tissues and the need for surgical removal can be avoided.

Degradable Linking Agent

As discussed above, the degradable linking agent includes one or more photoreactive groups attached to a linking group. The degradable linking agent can be represented by the formula Photo$^1$-LG-Photo$^2$, wherein Photo$^1$ and Photo$^2$ independently represent at least one photoreactive group and LG represents a linking group. The term "linking group" as used herein, refers to a segment or group of molecules configured to connect two or more molecule to each another, wherein the linking group is capable of degrading under one or more conditions. In one embodiment, the linking group includes at least one silicon atom. In another embodiment, the linking group includes at least one phosphorus atom.

The term "degradable linking group" as used herein, refers to a moiety configured to connect one molecule to another, wherein the linking group is capable of cleavage under one or more conditions. The term "biodegradable" as used herein, refers to degradation in a biological system, and includes for example, enzymatic degradation or hydrolysis. It should be noted that the term "degradable" as used herein includes both enzymatic and non-enzymatic (or chemical) degradation. It is also understood that hydrolysis can occur in the presence of or without an acid or base. In one embodiment, the linking agent is water soluble. In another embodiment, the linking agent is not water soluble.

In addition to providing a degradable bond, the linking group can function as a spacer, for example, to increase the distance between the photoreactive groups of the linking agent. For example, in some instances it may be desirable to provide a spacer to reduce steric hindrance that may result between the photoreactive groups, which could interfere with the ability of the photoreactive groups to form covalent bonds with a support surface, or from serving as a photoinitiator for polymerization. As described herein, it is possible to vary the distance between the photoreactive groups, for example, by increasing or decreasing the spacing between one or more photoreactive groups.

As described herein, one or more photoreactive groups can be bound to a linking group by a degradable linkage. In one embodiment, the degradable linkage between the photoreactive group and the linking group includes at least one heteroatom, including, but not limited to oxygen, nitrogen, selenium, sulfur or a combination thereof. In one embodiment, a photoreactive group, linking group and heteroatom form an ether (R$^1$—O—R$^2$), wherein R$^1$ is a photoreactive group and R$^2$ is a linking group. In another embodiment, a photoreactive group, linking group and heteroatom form an amine,

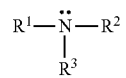

wherein R¹ is a photoreactive group, R² is a linking group, and R³ is hydrogen, aryl or alkyl, a photoreactive group, or a hydroxyl or salt thereof. In one embodiment, R³ is cyclic, linear or branched, saturated or unsaturated, aromatic or heteroaromatic, or a combination thereof. The stability of the ether and/or amine linkage can be influenced depending upon the size (e.g., chain length, branching, bulk, etc.) of the substituents. For example, bulkier substituents will generally result in a more stable linkage (i.e., a linking agent that is slower to degrade in the presence of water and/or acid).

In one embodiment, the linking group includes one or more silicon atoms. In a particular embodiment, the linking group includes one silicon atom (which can be referred to as a monosilane) covalently bound to at least two photoreactive groups. In another embodiment, the linking group includes at least two silicon atoms (which can be referred to as a disilane). In one embodiment, the linking group can be represented by the formula Si—Y—Si, wherein Y represents a linker that can be null (e.g., the linking group includes a direct Si—Si bond), an amine, ether, linear or branched $C_1$-$C_{10}$ alkyl, or a combination thereof. In one embodiment, Y is selected from O, $CH_2$, $OCH_2CH_2O$ and $O(CH_2CH_2O)_n$, wherein n is an integer between 1 and 5, between 1 and 10, between 1 and 15, between 1 and 20, between 1 and 25, or between 1 and 30. One embodiment of a disilane linking agent is shown below

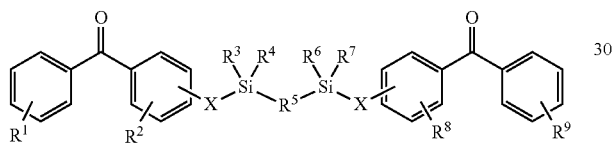

wherein R¹, R², R⁸ and R⁹ can be any substitution, including, but not limited to H, alkyl, halide, hydroxyl, amine, or a combination thereof; R³, R⁴, R⁶ and R⁷ can be alkyl, aryl or a combination thereof; R⁵ can be any substitution, including but not limited to O, alkyl or a combination thereof; and each X, independently, can be O, N, Se, S, or alkyl, or a combination thereof. One specific embodiment is shown below:

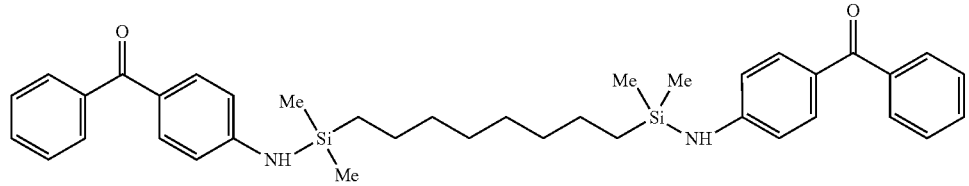 [SMILES: C[Si](C)(CCCCCCCC[Si](C)(C)Nc1ccc(C(=O)c2ccccc2)cc1)Nc1ccc(C(=O)c2ccccc2)cc1]

In one embodiment, the degradable linking agent can be represented by the formula

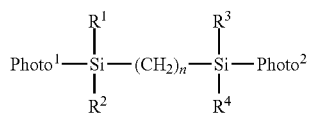

wherein Photo¹ and Photo², independently, represent one or more photoreactive groups and n is an integer between 1 and 10, wherein the degradable linking agent comprises a covalent linkage between at least one photoreactive group and the linking group, wherein the covalent linkage between at least one photoreactive group and the linking group is interrupted by at least one heteroatom. In general, a longer hydrocarbon chain between the two silicon atoms will tend to increase the flexibility of the linking agent and may facilitate crosslinking between a greater number of polymers than a linking agent with a shorter carbon chain, since the photoreactive groups can react with polymers located farther apart from one another. In the formula shown above, R¹, R², R³, R⁴ are independently alkyl or aryl, including, but not limited to cyclic, linear or branched, saturated or unsaturated, aromatic or heteroaromatic, or a combination thereof. In a more particular embodiment, R¹-R⁴ are independently phenyl, methyl, ethyl, isopropyl, t-butyl, or a combination thereof. In another embodiment, R¹-R⁴ can also be, independently, a photoreactive group. In yet another embodiment, R¹-R⁴ can also be, independently, hydroxyl or salt thereof. In one embodiment, the hydroxyl salt includes a counterion that is lithium, sodium, potassium, or a combination thereof.

In another embodiment, the linking agent can be represented by the formula

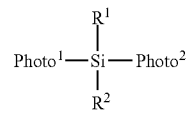

wherein Photo¹ and Photo², independently, represent one or more photoreactive group, wherein the degradable linking agent comprises a covalent linkage between at least one photoreactive group and the linking group, wherein the covalent linkage between at least one photoreactive group and the linking group is interrupted by at least one heteroatom; R¹ and R² are independently alkyl or aryl, including, but not limited to cyclic, linear or branched, saturated or unsaturated, aromatic or heteroaromatic, or a combination thereof. In a more particular embodiment, R¹ and R² are independently phenyl, methyl, ethyl, isopropyl, t-butyl, or a combination thereof. R¹ and R² can also be, independently, a photoreactive group, wherein the degradable linking agent comprises a covalent linkage between at least one photoreactive group and the linking group, wherein the covalent linkage between at least one photoreactive group and the linking group is interrupted by at least one heteroatom; or hydroxyl or salt thereof. In one embodiment, the hydroxyl salt includes a counterion that is lithium, sodium, potassium, or a combination thereof. One embodiment of a monosilane linking agent is shown below

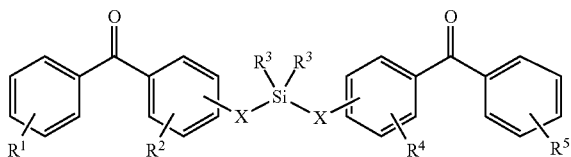

in which $R^1$ and $R^5$ can be any substitution, including, but not limited to H, halogen, amine, hydroxyl, alkyl, or a combination thereof; $R^2$ and $R^4$ can be any substitution, except OH, including, but not limited to H, alkyl or a combination thereof; $R^3$ can be alkyl, aryl or a combination thereof, including, for example, methyl, ethyl, propyl, isopropyl and butyl; and X, independently, can be O, N, Se, S, alkyl or a combination thereof.

In another embodiment, the linking group includes one or more phosphorous atoms. In one embodiment, the linking group includes one phosphorus atom (which can also be referred to as a mono-phosphorus linking group). In another embodiment, the linking agent includes two phosphorus atoms (which can also be referred to as a bis-phosphorus linking group). In one embodiment, the linking group comprises at least one phosphorus atom with a phosphorus-oxygen double bond (P=O), wherein at least one or two photoreactive groups are bound to the phosphorus atom. In another embodiment, the linking group comprises one phosphorus atom with a phosphorus-oxygen double bond (P=O), wherein two or three photoreactive groups are covalently bound to the phosphorus atom. In another embodiment, the linking group comprises at least two phosphorus atoms, wherein at least one phosphorus atom includes a phosphorus-oxygen double bond (P=O), and at least one or two photoreactive groups are covalently bound to each phosphorus atom.

In a more particular embodiment, the linking agent can be represented by the formula:

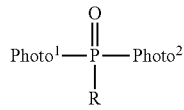

wherein $Photo^1$ and $Photo^2$, independently, represent one or more photoreactive groups, wherein the degradable linking agent comprises a covalent linkage between at least one photoreactive group and the linking group, wherein the covalent linkage between at least one photoreactive group and the linking group is interrupted by at least one heteroatom and R is alkyl or aryl, a photoreactive group, hydroxyl or salt thereof, or a combination thereof. In one embodiment, the hydroxyl salt includes a counterion that is lithium, sodium, potassium, or a combination thereof. In a more particular embodiment, R is cyclic, linear or branched, saturated or unsaturated, aromatic or heteroaromatic, or a combination thereof. In a more particular embodiment, R is phenyl, methyl, ethyl, isopropyl, t-butyl, or a combination thereof.

In another embodiment, the degradable linking agent can be represented by formula:

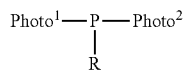

wherein $Photo^1$ and $Photo^2$ independently, represent one or more photoreactive groups, wherein the degradable linking agent comprises a covalent linkage between at least one photoreactive group and the linking group, wherein the covalent linkage between at least one photoreactive group and the linking group is interrupted by at least one heteroatom and R is alkyl or aryl, a photoreactive group (wherein the covalent linkage between the photoreactive group and the linking group may be interrupted by at least one heteroatom), hydroxyl or salt thereof, or a combination thereof. In one embodiment, the hydroxyl salt includes a counterion that is lithium, sodium, potassium, or a combination thereof. In a more particular embodiment, R is cyclic, linear or branched, saturated or unsaturated, aromatic or heteroaromatic, or a combination thereof. In one embodiment, R is phenyl, methyl, ethyl, isopropyl, t-butyl, or a combination thereof.

In another embodiment, the degradable linking agent can be represented by the formula:

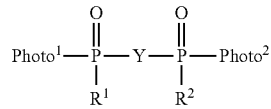

wherein $Photo^1$ and $Photo^2$, independently, represent one or more photoreactive groups, wherein the degradable linking agent comprises a covalent linkage between at least one photoreactive group and the linking group, wherein the covalent linkage between at least one photoreactive group and the linking group is interrupted by at least one heteroatom; Y represents a linker that can be null (i.e., not present, such that the linking group includes a direct P—P bond), N or O, linear or branched $C_1$-$C_{10}$ alkyl, or a combination thereof; and $R^1$ and $R^2$ are independently alkyl, aryl, a photoreactive group (wherein the covalent linkage between the photoreactive group and the linking group can be interrupted by at least one heteroatom), hydroxyl or salt thereof, or a combination thereof. In one embodiment, Y is selected from O, $CH_2$, $OCH_2O$, $OCH_2CH_2O$ and $O(CH_2CH_2O)_n$, wherein n is an integer between 1 and 5, between 1 and 10, between 1 and 15, between 1 and 20, between 1 and 25, or between 1 and 30. In one embodiment, the hydroxyl salt counterion is lithium, sodium, potassium, or a combination thereof. In a more particular embodiment, $R^1$ and $R^2$ are independently, cyclic, linear or branched hydrocarbon, saturated or unsaturated, aromatic or heteroaromatic, or a combination thereof. In one embodiment, $R^1$ and $R^2$ are independently phenyl, methyl, ethyl, isopropyl, t-butyl, or a combination thereof. In general, a longer hydrocarbon chain between the two phosphorus atoms will tend to increase the flexibility of the linking agent and may facilitate crosslinking between a greater number of polymers than a linking agent with a shorter carbon chain, since the reactive photoreactive groups can react with polymers located farther apart from one another. In one embodiment, Y can be O, $CH_2$, $OCH_2CH_2O$ and $O(CH_2CH_2O)_n$ wherein n is an integer between 1 and 5, between 1 and 10, between 1 and 15, between 1 and 20, between 1 and 25, or between 1 and 30.

One embodiment is shown below

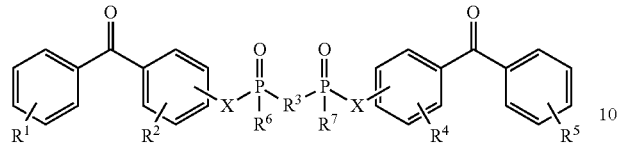

in which $R^1$, $R^2$, $R^4$ and $R^5$ can be any substitution, including but not limited to H, alkyl, halogen, amine, hydroxyl, or a combination thereof; $R^3$ can be any substitution, including but not limited to O, alkyl, or a combination thereof; and each X can independently be O, N. Se, S, alkyl, or a combination thereof. In one embodiment, the linking agent includes one or more phosphorester bonds and one or more phosphoramide bonds, and can be represented by the formula:

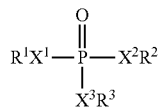

wherein X and $X^2$ are, independently, O, N, Se, S or alkyl; $R^1$ and $R^2$ are independently, one or more photoreactive groups, and $X^3$ is O, N, Se, S, alkyl or aryl; $R^3$ is alkyl or aryl, including, but not limited to cyclic, linear or branched, saturated or unsaturated, aromatic or heteroaromatic, or a combination thereof. In a more particular embodiment, $R^3$ is phenyl, methyl, ethyl, isopropyl, t-butyl, or a combination thereof. $R^3$ can also be a photoreactive group or a hydroxyl or salt thereof. In one embodiment, the hydroxyl salt counterion is lithium, sodium, potassium, or a combination thereof.

In one embodiment, the linking agent comprises a triphosphorester, which can be represented by the formula.

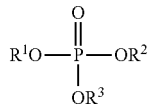

wherein $R^1$ and $R^2$ are independently, one or more photoreactive groups, and $R^3$ is alkyl or aryl, including, but not limited to cyclic, linear or branched, saturated or unsaturated, aromatic or heteroaromatic, or a combination thereof. In a more particular embodiment, $R^3$ is phenyl, methyl, ethyl, isopropyl, t-butyl, or a combination thereof. $R^3$ can also be a photoreactive group or hydrogen, or a hydroxyl salt. In one embodiment, the hydroxyl salt counterion is lithium, sodium, potassium, or a combination thereof.

Some specific embodiments include the following linking agents:
(a) bis(4-benzoylphenyl)hydrogen phosphate:

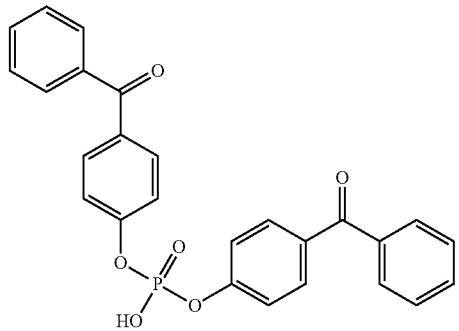 [SMILES: O=C(c1ccccc1)c1ccc(OP(=O)(O)Oc2ccc(C(=O)c3ccccc3)cc2)cc1]

(b) sodium bis(4-benzoylphenyl phosphate):

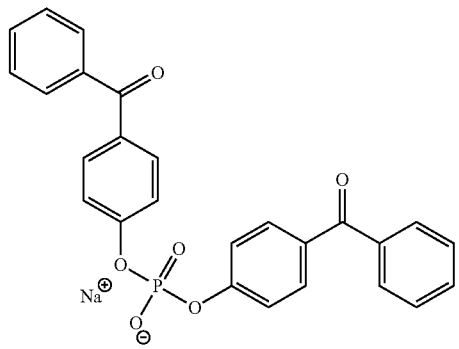 [SMILES: O=C(c1ccccc1)c1ccc(OP(=O)([O-])Oc2ccc(C(=O)c3ccccc3)cc2)cc1 ; [Na+]]

(c) tris(4-benzoylphenyl) phosphate:

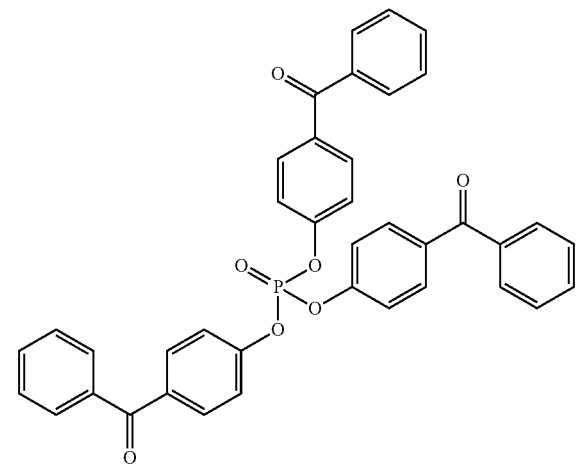 [SMILES: O=C(c1ccccc1)c1ccc(OP(=O)(Oc2ccc(C(=O)c3ccccc3)cc2)Oc2ccc(C(=O)c3ccccc3)cc2)cc1]

(d) tetrakis(4-benzoylphenyl)methylenebis(phosphonate)

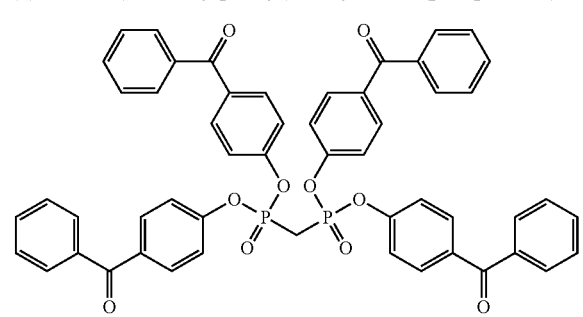 [SMILES: O=C(c1ccccc1)c1ccc(OP(=O)(CP(=O)(Oc2ccc(C(=O)c3ccccc3)cc2)Oc2ccc(C(=O)c3ccccc3)cc2)Oc2ccc(C(=O)c3ccccc3)cc2)cc1]

In another embodiment, the linking agent comprises a triphosphoramide, which can be represented by the formula.

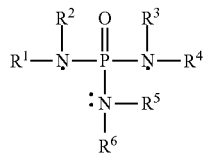

wherein $R^1$-$R^6$ are independently, a photoreactive group, a hydroxyl or salt thereof, alkyl or aryl, or a combination thereof, wherein at least two of $R^1$-$R^6$ are, independently, a photoreactive group. In one embodiment, the hydroxyl salt counterion is lithium, sodium, potassium, or a combination thereof. In a more particular embodiment, $R^1$-$R^6$ are independently cyclic, linear or branched, saturated or unsaturated, aromatic or heteroaromatic, or a combination thereof. In a more particular embodiment, $R^1$-$R^6$ are, independently, phenyl, methyl, ethyl, isopropyl, t-butyl, or a combination thereof.

Linking Element

The degradable linking agent can be formed using any suitable reaction pathway. In one embodiment, the degradable linking agent is formed by reacting a functionalized linking element with one or more, typically two or more photoreactive groups. As used herein, the term "linking element" refers to the linking group component of the degradable linking agent before it is bonded to one or more photoreactive groups. The term "functionalized linking element" is used to indicate that the linking element includes one or more reactive functional groups. In one embodiment, the linking element includes one or more halogen functional groups. The term "halogen" refers to fluorine, chlorine, bromine, or iodine functional groups. In another embodiment, the linking element includes one or more trifluoromethanesulfonate ($CF_3SO_3$—) functional groups.

In one embodiment, the linking element includes one or more silicon atoms. In one embodiment, the linking element includes one or more halogen substituents, such as fluorine, chlorine, bromine, iodine, and combinations thereof. In another embodiment, the linking element includes at least two halogen substituents. In another embodiment, the linking element includes one or more trifluoromethanesulfonate (triflate) substituents. In another embodiment, the linking element includes at least two triflate substituents. In a more particular embodiment, the linking element includes one silicon atom with at least two halogen or triflate substituents. In another embodiment, the linking element includes at least two silicon atoms. In a more particular embodiment, the linking element includes two silicon atoms, wherein each silicon atom includes at least one halogen or triflate substituent. In one embodiment, the linking element can be represented by the formula Si—Y—Si, wherein Y represents a linker that can be null, an amine, ether, linear or branched $C_1$-$C_{10}$ alkyl, or a combination thereof, wherein each silicon atom includes at least one halogen or triflate substituent. In one embodiment, Y is selected from O, $CH_2$, $OCH_2CH_2O$ and $O(CH_2CH_2O)_n$, wherein n is an integer between 1 and 5, between 1 and 10, between 1 and 15, between 1 and 20, between 1 and 25, or between 1 and 30.

In one embodiment, the linking element can be represented by the formula

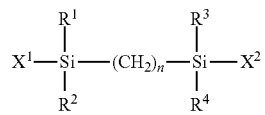

wherein $X^1$ and $X^2$ are independently halogen, such as fluorine, chlorine, bromine, iodine; trifluoromethanesulfonate; or a combination thereof and n is an integer between 1 and 10. $R_1$-$R_4$ are independently alkyl or aryl, including, but not limited to cyclic, linear or branched, saturated or unsaturated, aromatic or heteroaromatic, or a combination thereof. In a more particular embodiment, $R^1$-$R^4$ are independently phenyl, methyl, ethyl, isopropyl, t-butyl, or a combination thereof. In another embodiment, $R^1$-$R^4$ can also be, independently, halogen. In yet another embodiment, $R^1$-$R^4$ can also be, independently, hydroxyl or salt thereof. In one embodiment, the hydroxyl salt includes a counterion that is lithium, sodium, potassium, or a combination thereof.

In another embodiment, the linking element can be represented by the formula

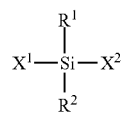

wherein $X^1$ and $X^2$ are independently halogen; such as fluorine, chlorine, bromine, and iodine; or trifluoromethanesulfonate; $R^1$ and $R^2$ are independently alkyl or aryl, including, but not limited to cyclic, linear or branched, saturated or unsaturated, aromatic or heteroaromatic, or a combination thereof. In a more particular embodiment, $R^1$ and $R^2$ are independently phenyl, methyl, ethyl, isopropyl, t-butyl, or a combination thereof. $R^1$ and $R^2$ can also be, independently, halogen, hydroxyl or hydroxyl salt. In one embodiment, the hydroxyl salt includes lithium, sodium, potassium, or a combination thereof as a counterion.

In another embodiment, the linking element includes one or more phosphorous atoms. In one embodiment, the linking element comprises at least one phosphorus atom with a phosphorus-oxygen double bond (P=O), wherein at least one halogen or trifluoromethanesulfonate substituent is bound to at least one phosphorus atom. In another embodiment, the linking element comprises one phosphorus atom with a phosphorus-oxygen double bond (P=O), wherein two or three halogen or trifluoromethanesulfonate substituents are, independently, covalently bound to the phosphorus atom. In another embodiment, the linking element comprises at least two phosphorus atoms, wherein at least one phosphorus atom includes a phosphorus-oxygen double bond (P=O), and at least one or two halogen or trifluoromethanesulfonate substituents are covalently bound to each phosphorus atom. In a more particular embodiment, the linking element comprises two phosphorus atoms.

In a more particular embodiment, the linking element can be represented by the formula

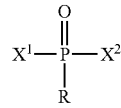

wherein $X^1$ and $X^2$ are independently halogen; such as fluorine, chlorine, bromine, and iodine; or trifluoromethanesulfonate; and R is alkyl or aryl, halogen, hydroxyl or a hydroxyl salt, or a combination thereof. In one embodiment, the hydroxyl salt includes a counterion that is lithium, sodium, potassium, or a combination thereof. In a more particular embodiment, R is cyclic, linear or branched, saturated or unsaturated, aromatic or heteroaromatic, or a combination thereof. In a more particular embodiment, R is phenyl, methyl, ethyl, isopropyl, t-butyl, or a combination thereof.

In another embodiment, the degradable linking element can be represented by formula:

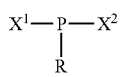

wherein $X^1$ and $X^2$ are independently halogen, such as fluorine, chlorine, bromine, and iodine; or trifluoromethanesulfonate and R is alkyl or aryl, halogen, trifluoromethanesulfonate, hydroxyl or salt thereof, or a combination thereof. In one embodiment, the hydroxyl salt includes a counterion that is lithium, sodium, potassium, or a combination thereof. In a more particular embodiment, R is cyclic, linear or branched, saturated or unsaturated, aromatic or heteroaromatic, or a combination thereof. In one embodiment, $R^1$ and $R^2$ are independently phenyl, methyl, ethyl, isopropyl, t-butyl, or a combination thereof.

In another embodiment, the degradable linking element can be represented by the formula:

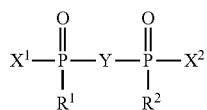

wherein $X^1$ and $X^2$ are independently halogen, such as fluorine, chlorine, bromine, and iodine; or trifluoromethanesulfonate, Y represents a linker that can be null, an amine, an ether, linear or branched $C_1$-$C_{10}$ alkyl, or a combination thereof; and $R^1$ and $R^2$ are independently alkyl, aryl, halogen, hydroxyl or salt thereof, or a combination thereof. In one embodiment, Y is selected from O, $CH_2$, $OCH_2CH_2O$ and $O(CH_2CH_2O)_n$, wherein n is an integer between 1 and 5, between 1 and 10, between 1 and 15, between 1 and 20, between 1 and 25, or between 1 and 30. In one embodiment, the hydroxyl salt counterion is lithium, sodium, potassium, or a combination thereof. In a more particular embodiment, $R^1$ and $R^2$ are independently, cyclic, linear or branched hydrocarbon, saturated or unsaturated, aromatic or heteroaromatic, or a combination thereof. In one embodiment, $R^1$ and $R^2$ are independently phenyl, methyl, ethyl, isopropyl, t-butyl, or a combination thereof.

Methods of Making

The degradable linking agent can be formed using any suitable reaction pathway. In one embodiment, the degradable linking agent is formed by reacting a halogenated or triflated linking element with one or more, typically two or more photoreactive groups, for example, by a nucleophilic substitution reaction. As used herein, the term "linking element" refers to the linking group component of the degradable linking agent before it is bonded to a photoreactive group. As used herein, the term "halogenated" refers to the presence of one or more halogen substituents, including fluorine, chlorine, bromine, or iodine, which can, under the appropriate conditions, serve as a leaving group in a nucleophilic substitution reaction. As used herein, the term triflated, refers to the presence of one or more trifluoromethanesulfonate ($CF_3SO_3$—) functional groups that can, under the appropriate conditions, serve as a leaving group in an nucleophilic substitution reactions.

Figure 2:
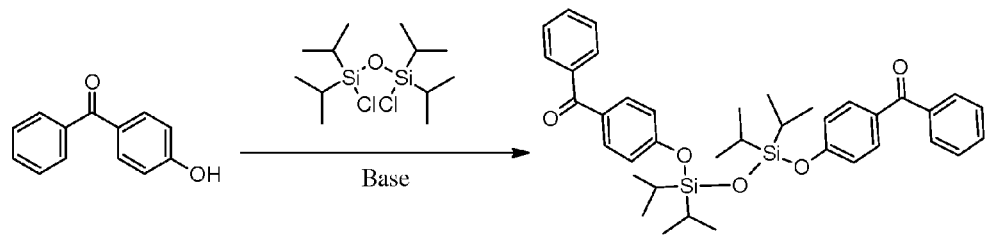
FIG. 2 shows a reaction pathway for the generation of a degradable linking agent as described herein.
Figure 3:
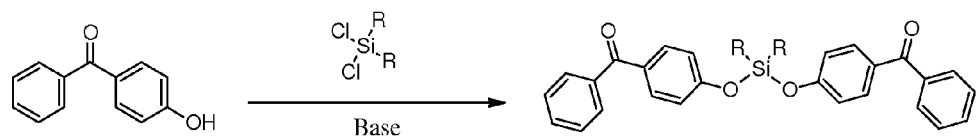
FIG. 3 shows a reaction pathway for the generation of a degradable linking agent as described herein.
Figure 4:
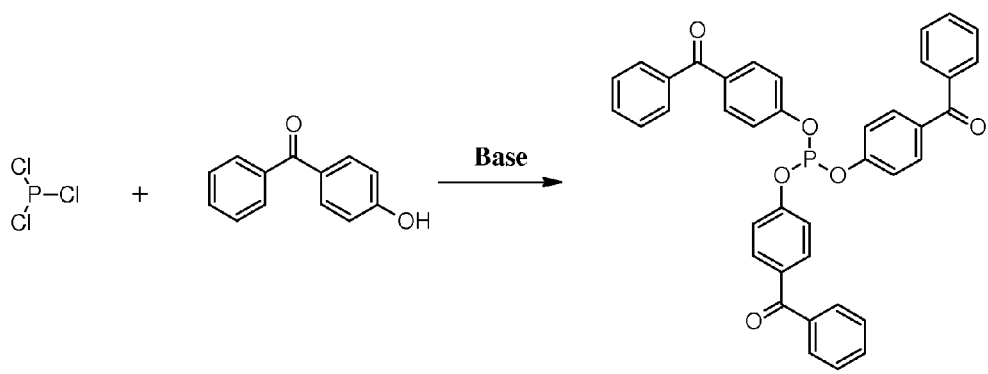
FIG. 4 shows a reaction pathway for the generation of a degradable linking agent as described herein.
Figure 5:
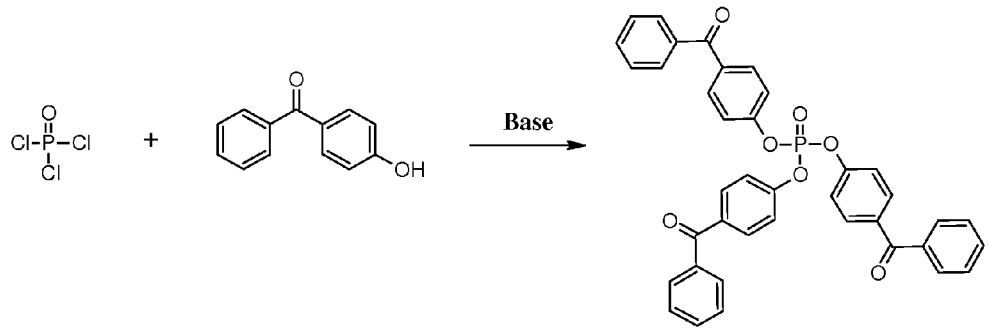
FIG. 5 shows a reaction pathway for the generation of a degradable linking agent as described herein.
Figure 6:
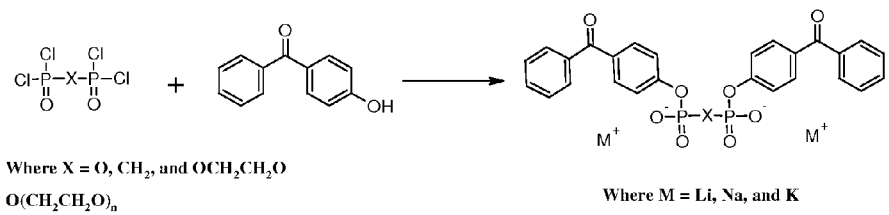
FIG. 6 shows a reaction pathway for the generation of a degradable linking agent as described herein.
Figure 7:
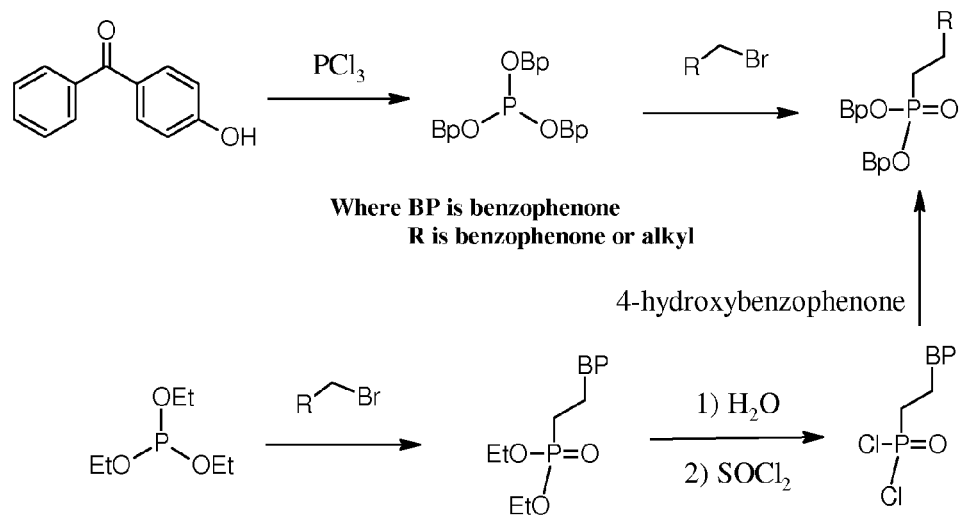
FIG. 7 shows a reaction pathway for the generation of a degradable linking agent as described herein.
Figure 8:
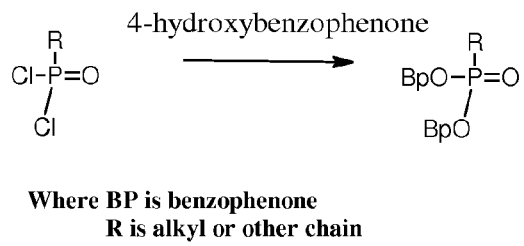
FIG. 8 shows a reaction pathway for the generation of a degradable linking agent as described herein.

Examples of nucleophilic substitution reactions include, but are not limited to the following. In one embodiment, a degradable linking agent is formed by connecting two molecules of 4-hydroxybenzophenone with a halogenated disilane linking element by a nucleophilic substitution reaction to form a degradable linking agent as shown in FIG. 1. In another embodiment, a degradable linking agent is formed by connecting two molecules of 4-hydroxybenzophenone with a halogenated di-silyl linking element by a nucleophilic substitution reaction to form a degradable linking agent as shown in FIG. 2. In yet another embodiment, a degradable linking agent is formed by connecting two molecules of 4-hydroxybenzophenone with a dichlorosilane linking element by a nucleophilic substitution reaction to form a degradable linking agent as shown in FIG. 3. In another embodiment, a degradable linking agent is formed by reacting phosphorous trichloride with 4-hydroxybenzophenone in a presence of base such as pyridine or diisopropylethyl amine as shown in FIG. 4. In another embodiment, a degradable linking agent is formed by reacting phosphoryl chloride with 4-hydroxybenzophenone in a presence of a base such as pyridine or diisopropylethyl amine as shown in FIG. 5. In another embodiment, a degradable linking agent is formed by reacting diphosphorous halide with 4-hydroxybenzophenone as shown in FIG. 6. In another embodiment, a degradable linking agent is formed by converting 4-hydroxybenzophenone into its phosphite derivative by reacting the hydroxybenzophenone with $PCl_3$. The resulting phosphite is reacted with halide, such as chlorine, using Michaelis-Arbusov conditions to generate the degradable linking agent as shown in FIG. 7. In an alternate pathway, the degradable linking agent is formed using phosphite as a starting material as shown in FIG. 8.

Photoreactive Groups

As used herein, the term "photoreactive group" refers to a molecule having one or more functional groups that are capable of responding to a specific applied external stimulus to undergo active specie generation and form a covalent bond with an adjacent chemical structure, which can be provided by the same or a different molecule. Photoreactive groups are those groups of atoms in a molecule that retain their covalent bonds unchanged under conditions of storage but that, upon activation by an external energy source, form one or more covalent bonds with other molecules. In one embodiment, the photoreactive groups can generate active species such as free radicals upon absorption of electromagnetic energy. Photoreactive groups can be chosen to be responsive to various portions of the electromagnetic spectrum, including, for example, the ultraviolet and visible portions of the spectrum. Photoreactive groups are described, for example, in U.S. Pat. No. 5,002,582, the disclosure of which is incorporated herein by reference.

In one embodiment, the photoreactive group includes a substituent capable of reacting with halogenated or triflated linking element. In a more particular embodiment, the photoreactive group contains a hydroxyl (—OH) or amine (—NR$_2$) substituent, wherein the amine substituent can be a primary amine or a secondary amine.

In one embodiment, the functionalized photoreactive group can be represented by the formula Photo-Y—OH, wherein Y represents a linker that can be null, an amine, an ether, linear or branched C$_1$-C$_{10}$ alkyl, or a combination thereof. In one embodiment, Y is selected from O, CH$_2$, OCH$_2$CH$_2$O and O(CH$_2$CH$_2$O)$_n$, wherein n is an integer between 1 and 5, between 1 and 10, between 1 and 15, between 1 and 20, between 1 and 25, or between 1 and 30. In another embodiment, the functionalized photoreactive group can be represented by the formula

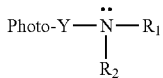

wherein Y represents a linker that can be null, an amine, an ether, linear or branched C$_1$-C$_{10}$ alkyl, or a combination thereof and R$_1$ and R$_2$ are independently alkyl or aryl, including, but not limited to cyclic, linear or branched, saturated or unsaturated, aromatic or heteroaromatic, or a combination thereof. In a more particular embodiment, R$_1$ and R$_2$ are independently phenyl, methyl, ethyl, isopropyl, t-butyl, or a combination thereof. In one embodiment, Y is selected from O, CH$_2$, OCH$_2$CH$_2$O and O(CH$_2$CH$_2$O)$_n$, wherein n is an integer between 1 and 5, between 1 and 10, between 1 and 15, between 1 and 20, between 1 and 25, or between 1 and 30.

In one embodiment, the halogenated linking element reacts with the amine or hydroxyl substituent on the photoreactive group to provide a degradable linking agent. One advantage of a photoreactive group with a reactive amine substituent, is that the amine substituent is able to react with additional halogen substituents on other linking elements, which can result in the amine substituent of a first photoreactive group binding to more than one linking element. For example, a first photoreactive group can be attached to a first linking group by a first amine and a second photoreactive group can then be attached to the first linking agent and the first photoreactive group by the same (first) amine. If desired, the degradable linking agent can also include a third photoreactive group attached to the first linking group by a second amine and, if desired, a fourth photoreactive group can also be attached to the first linking agent and the third photoreactive group by the second amine. One example is shown below, wherein R independently, can be alkyl or aryl, including but not limited to cyclic, linear or branched, saturated or unsaturated, aromatic or heteroaromatic, or a combination thereof. In a more particular embodiment, R can be, independently, a photo reactive group, wherein the covalent linkage between the photoreactive group and the linking group is interrupted by at least one heteroatom; phenyl, methyl, ethyl, isopropyl, t-butyl, or a combination thereof:

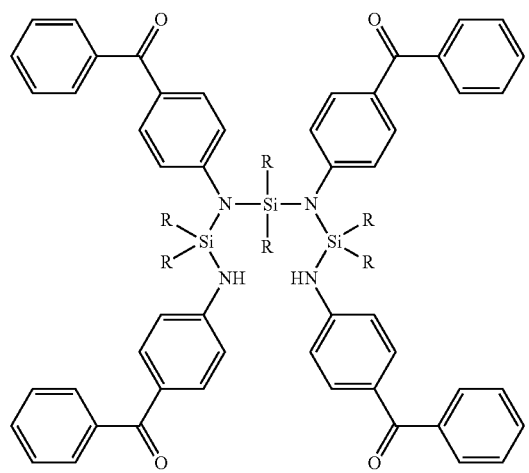

In one embodiment, the photoreactive group includes a photoreactive aryl ketone, such as acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. Examples of aryl ketones include heterocyclic derivatives of anthrone, including acridone, xanthone, and thioxanthone, and their ring substituted derivatives. One example includes thioxanthone, and its derivatives, having excitation energies greater than about 360 nm. In one embodiment, the photoreactive group is a functionalized benzophenone with an amine or hydroxyl substituent at positions 3 or 4 (i.e., 3- or 4-aminobenzophenone or 3- or 4-hydroxybenzophenone). As discussed above, the functionalized benzophenone can include a linker between the benzophenone photoreactive group and the amine or hydroxyl substituent. Examples of linkers include an amine, an ether, linear or branched C$_1$-C$_{10}$ alkyl, or a combination thereof.

The functional groups of such ketones are readily capable of undergoing the activation/inactivation/reactivation cycle described herein. Benzophenone is one example of a photoreactive moiety that is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Photoactivatable aryl ketones such as benzophenone and acetophenone are subject to multiple reactivation in water and may increase coating efficiency.

The azides constitute one class of photoreactive groups and include derivatives based on arylazides (C$_6$R$_5$N$_3$) such as phenyl azide and particularly 4-fluoro-3-nitrophenyl azide, acyl azides (—CO—N$_3$) such as benzoyl azide and p-methylbenzoyl azide, azido formates (—O—CO—N$_3$) such as ethyl azidoformate, phenyl azidoformate, sulfonyl azides (—SO$_2$—N$_3$) such as benzenesulfonyl azide, and phosphoryl azides (RO)$_2$PON$_3$ such as diphenyl phosphoryl azide and diethyl phosphoryl azide. Diazo compounds constitute another class of photoreactive groups and include derivatives of diazoalkanes (—CHN$_2$) such as diazomethane and diphenyldiazomethane, diazoketones (—CO—CHN$_2$) such as diazoacetophenone and 1-trifluoromethyl-1-diazo-2-pentanone, diazoacetates (—O—CO—CHN$_2$) such as t-butyl diazoacetate and phenyl diazoacetate, and beta-keto-alpha-diazoacetates (—CO—CN$_2$—CO—O—) such as t-butyl alpha diazoacetoacetate. Other photoreactive groups include the diazirines (—CHN$_2$) such as 3-trifluoromethyl-3-phenyldiazirine, and ketenes (—CH=C=O) such as ketene and diphenylketene.

Upon activation of the photoreactive groups, the linking agents are covalently bound to each other, to other molecules, or to a surface by covalent bonds through residues of the photoreactive groups. Exemplary photoreactive groups, and their residues upon activation, are shown as follows.

| Photoreactive | Group |
| --- | --- |
| aryl azides | amine (R—NH—R') |
| acyl azides | amide (R—CO—NH—R') |
| azidoformates | carbamate (R—O—CO—NH—R') |
| sulfonyl azides | sulfonamide (R—SO$_2$—NH—R') |
| phosphoryl azides | phosphoramide ((RO)$_2$PO—NH—R') |
| diazoalkanes | new C—C bond |
| diazoketones | new C—C bond and ketone |
| diazoacetates | new C—C bond and ester |
| beta-keto-alpha- diazoacetates | new C—C bond and beta-ketoester |
| aliphatic azo | new C—C bond |
| diazirines | new C—C bond |
| ketenes | new C—C bond |
| photoactivated ketones | new C—C bond and alcohol |

Photoinitiation of free radicals can take place via various mechanisms, including photochemical intramolecular photocleavage, hydrogen abstraction, and redox reactions. In one embodiment, photoinitiation takes place by hydrogen abstraction from the polymerizable groups.

Intramolecular photocleavage involves a homolytic alpha cleavage reaction between a carbonyl group and an adjacent carbon atom. This type of reaction is generally referred to as a Norrish type I reaction. Examples of molecules exhibiting Norrish type I reactivity and useful in a polymeric initiating system include derivatives of benzoin ether and acetophenone. For example, in one embodiment wherein the linking agent is provided in the form of a quinone having adjacent carbonyl groups (e.g., camphorquinone), photoinitiation takes place via intramolecular bond cleavage.

A second mechanism, hydrogen abstraction, can be either intra- or intermolecular in nature. A system employing this mechanism can be used without additional energy transfer acceptor molecules and by nonspecific hydrogen abstraction. However, this system is more commonly used with an energy transfer acceptor, typically a tertiary amine, which results in the formation of both aminoalkyl radicals and ketyl radicals. Examples of molecules exhibiting hydrogen abstraction reactivity and useful in a polymeric initiating system, include analogs of benzophenone and camphorquinone.

A third mechanism involves photosensitization reactions utilizing photoreducible or photo-oxidizable dyes. In most instances, photoreducible dyes are used in conjunction with a reductant, typically a tertiary amine. The reductant intercepts the induced triplet producing the radical anion of the dye and the radical cation of the reductant.

In one embodiment, photoinitiation generates active species such as free radicals, including nitrenes, carbenes, and excited states of ketones upon absorption of electromagnetic energy. This excited photoinitiator in turn abstracts hydrogen atoms from available sources in proximity to the photoinitiator, e.g., polymerizable species, applied to the primed surface. This hydrogen abstraction thus generates a free radical site within the polymerizable species from which polymerization can proceed.

A typical free radical polymerization includes four steps: initiation, propagation, and termination. In initiation, a free radical derived from an initiator adds to a monomer molecule to form an active center. Other initiating reactions include addition to the head of the molecule or hydrogen abstraction, and the reaction mechanism depends upon the structures of the radical and monomer. The propagation or growth reaction includes of the rapid addition of monomer molecules to the radical species. The most common mechanism of propagation occurs in head-to-tail fashion. However, propagation may also occur in head-to-head, tail-to-head, and tail-to-tail modes. In termination, the polymer chain stops growing by the destruction of propagating radicals. Normally, in the absence of species that destroy radicals, chain termination occurs by bimolecular interaction of radicals (e.g., radical combinations or disproportionation).

In one embodiment, the linking agent includes a conjugated cyclic diketone having attached thereto, either directly or indirectly, one or more substituents including negatively charged groups, and wherein each ketone group of the diketone is adapted to serve as a photoreactive moiety capable of being activated in order to provide a free radical. In one embodiment, the conjugated cyclic diketone is a quinone selected from substituted and unsubstituted benzoquinone, camphorquinone, naphthoquinone, and anthraquinone.

Charged Groups

In one embodiment, the linking agent includes one or more charged groups to improve properties such as water solubility, hemocompatability and/or antithrombogenicity. As used herein, a "charged" group generally refers to a group that is present in ionic form in solution, i.e., carries an electrical charge under the conditions (e.g., pH) of use. The type and number of charged groups in a linking agent can vary. In one embodiment, the linking agent includes a sufficient number and type of charged groups to provide the agent with water solubility (at room temperature and optimal pH) of at least about 0.1 mg/ml, at least about 0.5 mg/ml, and at least about 1 mg/ml. In one embodiment, the linking agent is configured for use in a surface coating process and has a solubility level of at least about 0.1 mg/ml.

In one embodiment, one or more charged groups are introduced into the linking agent by the inclusion of a hydroxyl salt, such as a lithium, sodium, potassium salt, or a combination thereof on the linking agent.

Surface Modification

In one embodiment, the degradable linking agent is used to form a coating on a substrate surface. In one embodiment, the coating is hydrophobic. In another embodiment, the coating is hydrophilic. The coating can be formed in any suitable manner, e.g., by simultaneous or sequential attachment of the linking agent and chemical compounds (e.g., molecules bearing polymerizable groups) to a support surface. In one embodiment, the method involves a two step process, involving sequential steps in which linking agent is first attached to the surface, after which compounds are polymerized thereon using the photoinitator of the attached agent. One advantage of a sequential approach is that photopolymerization of this sort allows the generation of thin polymer layers on the support surface. The resultant polymer layer is typically highly adherent, uniform in thickness, and is highly durable. Moreover, solutions used to form the polymer layer can be applied (e.g., via in solution application, dip coating, spray coating, knife coating, and roller coating) to any suitable support surface of any surface morphology. The resultant polymer layer, in turn, can be adapted to cover irregular surfaces as well as smooth, relatively uniform surfaces. The polymerizable species can also be attached to the support surface simultaneously with the linking agent, by providing suitable reaction conditions to allow such simultaneous attachment of the linking agent and polymerization of the polymerizable species.

The photoinitiator group (i.e., the second photoreactive group, or latent reactive group) can be identical to, or different from, the first photoreactive group used to attach the linking agent to a support surface. In one embodiment, the first and second photoreactive groups are adapted to be independently activated by light of different wavelengths (e.g., ultraviolet light versus visible light).

Upon activation of the photoreactive groups in the presence of a support surface, the second photoreactive group(s) remain unbound to the support surface and revert to their inactive state (e.g., latent) in order to serve as photoinitiator groups. While not intending to be bound by theory, it appears that the ability of a photoreactive group to remain unbound (and hence serve as a photoinitiator) is a factor, at least in part, of various reaction conditions (e.g., time and intensity of illumination wavelength, reagent concentration, etc.) and/or restrictions imposed by the size and/or structure of the linking agent itself. The photoinitiator thus remains available to be subsequently activated by a suitable energy source, and thereby initiate photopolymerization.

In one embodiment, the linking agent described herein is applied to a surface having carbon-hydrogen bonds with which the photoreactive groups can react to immobilize the linking agents. In one embodiment, the support surface provides abstractable hydrogen atoms suitable for covalent bonding with the activated group. In another embodiment, the surface can be modified (e.g., by pretreatment with a suitable reagent) to provide abstractable hydrogen atoms on the surface.

The method described herein is suitable for use in connection with a variety of support surfaces, including hydrogel polymers, silicone, polypropylene, polystyrene, poly (vinyl chloride), polycarbonate, poly(methyl methacrylate), parylene and any of the numerous organosilanes used to pretreat glass or other inorganic surfaces. The photoreactive linking agents can be applied to surfaces in any suitable manner (e.g., in solution or by dispersion), then photoactivated by uniform illumination to immobilize them to the surface. Examples of suitable hydrogel polymers are selected from silicone hydrogels, hydroxyethylmethacrylate polymers, and glyceryl methacrylate polymers.

Other suitable surface materials include polyolefins, polystyrenes, poly(methyl)methacrylates, polyacrylonitriles, poly(vinylacetates), poly(vinyl alcohols), chlorine-containing polymers such as poly(vinyl) chloride, polyoxymethylenes, polycarbonates, polyamides, polyimides, polyurethanes, phenolics, amino-epoxy resins, polyesters, silicones, cellulose-based plastics, and rubber-like plastics. See generally, "Plastics," pp. 462-464, in Concise Encyclopedia of Polymer Science and Engineering, Kroschwitz, ed., John Wiley and Sons, 1990, the disclosure of which is incorporated herein by reference. In addition, supports such as those formed of pyrolytic carbon and silylated surfaces of glass, ceramic, or metal are suitable for surface modification.

Such materials can be used to fabricate a number of devices capable of being provided, either before, during and/or after their fabrication, with a polymer layer. Implant devices are one general class of suitable devices, and include, but are not limited to, vascular devices such as grafts, stents, catheters, valves, artificial hearts, and heart assist devices; orthopedic devices such as joint implants, fracture repair devices, and artificial tendons; dental devices such as dental implants and fracture repair devices; ophthalmic devices such as lenses and glaucoma drain shunts; and other catheters, synthetic prostheses and artificial organs. Other suitable biomedical devices include dialysis tubing and membranes, blood oxygenator tubing and membranes, blood bags, sutures, membranes, cell culture devices, chromatographic support materials, biosensors, and the like.

Surface modification can be achieved using photopolymerization (e.g., by free radical polymerization). In accordance with the present method, a selected surface is contacted with a linking agent, as described above. During and/or after application of the linking agent, the surface is illuminated with UV light of the appropriate wavelength, thereby activating the photoreactive groups. The linking agent is thus immobilized to the surface, by means of the first photoreactive groups (with the second photoreactive groups reverting to inactive form), and excess linking agent can then be optionally washed away, leaving a surface primed with a base layer of linking agent.

The linking agent can be applied to the surface of interest in any suitable manner. For example, the linking agent can be applied by dip coating or by dispersing the agent on the surface (for example, by spray coating). Suitable methods of application include application in solution, dip coating, spray coating, knife coating, and roller coating. In one embodiment, the linking agent is applied to the surface via spray coating, as this application method provides increased density of the linking agent on the support surface, thereby improving grafting durability.

In the sequential approach described herein, a solution containing polymerizable compounds can be applied to a primed surface. The solution can be illuminated in situ to activate the second photoreactive group(s) that serve as a photoinitiator(s), thus initiating free radical polymerization via hydrogen abstraction. In one embodiment, photopolymerization takes place in an inert atmosphere, since oxygen interferes with free radical polymerization. Deoxygenation can take place using an inert gas such as nitrogen.

Once the system has been deoxygenated, the surface can again be illuminated with UV light of the appropriate wavelength. This second illumination thus activates the second photoreactive group(s) serving as a photoinitiator(s) of free radical polymerization. In one embodiment, illumination generates the excited state of the photoreactive group, allowing the excited molecule to abstract a hydrogen from available sources, e.g., molecules bearing polymerizable groups. Such hydrogen abstraction generates a free radical site, from which polymerization can proceed.

The method includes steps of providing a support surface and applying a linking agent to the support surface. In one embodiment, the method further includes a step of illuminating the linking agent to photochemically attach the linking agent to the surface. In one embodiment, the method further includes a step of providing a plurality of molecules bearing free radical polymerizable groups and illuminating the molecules bearing polymerizable groups and the linking agent to initiate polymerization of the molecules bearing polymerizable groups on the support surface.

In one embodiment the linking agent is used in connection with a plurality of molecules, each bearing one or more polymerizable groups. In accordance with this embodiment, the photoreactive group serves as an initiator to initiate polymerization of the polymerizable groups. As used herein, "polymerizable group" refers to a group that is adapted to be polymerized by initiation via free radical generation, and by photoinitiators activated by visible or long wavelength ultraviolet radiation.

A variety of polymerizable compounds are suitable for use as with the linking agent described herein. In one embodiment, the polymerization products (e.g., a polymer layer resulting from free radical polymerization) is hydrophilic or is capable of being modified to provide hydrophilic characteristics at appropriate reaction conditions (e.g., pH). Moreover, the polymerizable groups of such compounds can include those adapted to participate in free-radical polymerization. In one embodiment, compounds include at least one free-radical polymerizable component (e.g., a vinyl group), and at least one functional group with a high affinity for water. Such functional groups with a high affinity for water can be negatively charged, positively charged, or electrically neutral.

Suitable polymerizable compounds are selected from monomeric polymerizable molecules (e.g., organic monomers), and macromeric polymerizable molecules (e.g., organic macromers). As used herein, "macromer" shall refer to a macromolecular monomer having a molecular weight of about 250 to about 25,000, and from about 1,000 to about 5,000.

Suitable polymerizable compounds can contain electrically neutral hydrophilic functional units, for example, acrylamide and methacrylamide derivatives. Examples of suitable monomers containing electrically neutral hydrophilic structural units include acrylamide, methacrylamide, N-alkylacrylamides (e.g., N,N-dimethylacrylamide or methacrylamide, N-vinylpyrrolidinone, N-vinylacetamide, N-vinyl formamide, hydroxyethylacrylate, hydroxyethylmethacrylate, hydroxypropyl acrylate or methacrylate, glycerolmonomethacrylate, and glycerolmonoacrylate).

Alternatively, suitable polymerizable compounds containing electrically neutral hydrophilic functional units include molecules whose polymers, once formed, can be readily modified (e.g., hydrolyzed by the addition of ethylene oxide) to provide products with enhanced affinity for water. Examples of suitable monomers of this type include glycidyl acrylate or methacrylate, whose polymers bear epoxy groups that can be readily hydrolyzed to provide glycol structures having a high affinity for water.

Examples of suitable monomeric polymerizable molecules that are negatively charged at appropriate pH levels include acrylic acid, methacrylic acid, maleic acid, fumaric acid, itaconic acid, AMPS (acrylamidomethylpropane sulfonic acid), vinyl phosphoric acid, vinylbenzoic acid, and the like.

Alternatively, suitable monomeric polymerizable molecules that are negatively charged at appropriate pH levels include molecules whose polymers, once formed, can be readily modified (e.g., by hydrolysis via the addition of ethylene oxide) to provide products with enhanced affinity for water. Examples of suitable monomers of this type include maleic anhydride, whose polymers bear anhydride groups that can be readily hydrolyzed to provide carboxylic acid groups, or can be readily reacted with amines to provide amide/acid structures with high affinity for water, and polymerized vinyl esters.

Examples of suitable monomeric molecules that are positively charged at appropriate pH levels include 3-aminopropylmethacrylamide (APMA), methacrylamidopropyltrimethylammonium chloride (MAPTAC), N,N-dimethylaminoethylmethacrylate, N,N-diethylaminoethylacrylate, and the like.

Alternatively, suitable positively charged monomeric polymerizable molecules include those molecules that can be readily modified (e.g., by hydrolysis via the addition of ethylene oxide) to provide products with enhanced affinity for water as well as a positive charge, e.g., glycidyl methacrylate whose polymeric products can be reacted with amines (e.g., ethylamine), to provide hydroxyamino compounds. In some cases, these materials will contain a structural unit with an inherent positive charge, as for example with fully quaternized ammonium structures. In other cases, the positively charged structural unit will exist at certain pH values, particularly at acidic pH values.

In an alternative embodiment, the polymerizable compounds include macromeric polymerizable molecules. Suitable macromers can be synthesized from monomers such as those illustrated above. According to one embodiment, polymerizable functional components (e.g., vinyl groups) of the macromer can be located at either terminus of the polymer chain, or at one or more points along the polymer chain, in a random or nonrandom structural manner.

The number of free-radical polymerizable groups per molecule can be varied according to the application. For example, a macromer with just one free-radical polymerizable unit can be used. In other instances, however, a macromer with more than one, e.g., two or more polymerizable units per macromer can be used. Additionally, the macromer can contain structural features to provide improved affinity for water in a manner typically unavailable in small molecule structures (e.g., hydrophilic poly(ethylene glycol) materials).

Examples of suitable macromeric polymerizable compounds include methacrylate derivatives, monoacrylate derivatives, and acrylamide derivatives. Macromeric polymerizable compounds include poly(ethylene glycol) monomethacrylate, methoxypoly(ethylene glycol) monomethacrylate, poly(ethylene glycol)monoacrylate, monomethyacrylamidopoly(acrylamide), poly(acrylamide-co-3-methacrylamidopropylacrylamide), poly(vinylalcohol) monomethacrylate, poly(vinylalcohol)monoacrylate, poly(vinylalcohol)dimethacrylate, and the like.

Such macromers can be prepared, for instance, by first synthesizing a hydrophilic polymer of the desired molecular weight, followed by a polymer modification step to introduce the desired level of polymerizable (e.g., vinyl) functional units. For example, acrylamide can be copolymerized with specific amounts of 3-aminopropylmethacrylamide comonomer, and the resulting copolymer can then be modified by reaction with methacrylic anhydride to introduce the methacrylamide functional units, thereby producing a useful macromer.

Poly(ethylene glycol) of a desired molecular weight can be synthesized or purchased from a commercial source, and modified (e.g., by reaction with methacrylyl chloride or methacrylic anhydride) to introduce the terminal methacrylate ester units to produce a suitable macromer. Some applications can benefit by use of macromers with the polymerizable units located at or near the terminus of the polymer chains, whereas other uses can benefit by having the polymerizable unit(s) located along the hydrophilic polymer chain backbone.

Such monomeric and macromeric polymerizable molecules can be used alone or in combination with each other, including for instance, combinations of macromers with other macromers, monomers with other monomers, or macromers combined with one or more small molecule monomers capable of providing polymeric products with the desired affinity for water. Moreover, the above polymerizable compounds can be provided in the form of amphoteric compounds (e.g., zwitterions), thereby providing both positive and negative charges.

Biodegradable Polymer Foams

In another embodiment, the linking agent can be used in connection with a composition that is capable of in situ polymerization. In one embodiment, the linking agent can be used in connection with a biocompatible, biodegradable polymer foam. Biodegradable foam used for the treatment of wounds are described, for example, in US Patent Publication No. 2009/0093550, the disclosure of which is hereby incorporated by reference herein in its entirety.

In one embodiment, a biodegradable foam is formed using an "application composition" that includes a polymerizable component, a polymerization initiator, and a gas-releasing component. Suitable polymerization initiators include photoinitiators, including the photoreactive groups of the linking agent described herein. An application composition can be used to form biocompatible foam in situ, or as a pre-formed foam.

The biocompatible polymer foams can be formed from macromers that include "polymerizable group(s)," which generally refers to chemical groups that are polymerizable in the presence of free radicals. A polymerizable group generally includes a carbon-carbon double bond, which can be an ethylenically unsaturated group or a vinyl group. Upon initiation of a polymerization reaction in the application composition, the polymerizable groups, are activated by free radical propagation in the composition, and covalently bonded with other polymerizable groups. As a result of the covalent bonding a crosslinked polymeric matrix is formed. Gas bubbles are generated in the application composition by foaming agents while polymerization of the macromers (which causes polymer matrix formation) is occurring. As a result, a foam is formed, with air pockets (also referred to herein as "cells") partially or completely surrounded by a wall of the crosslinked polymeric matrix.

Examples of polymerizable groups include, but are not limited to, acrylate groups, methacrylate groups, ethacrylate groups, 2-phenyl acrylate groups, acrylamide groups, methacrylamide groups, itaconate groups, and styrene groups. In some aspects the macromers of the invention include one or more methacrylate group(s).

Polymerizable groups can be "pendent" from the macromer at more than one location along the polymer backbone. In some cases the polymerizable groups are randomly located along the length of the polymer backbone. Such randomly spacing typically occurs when the macromer is prepared from a polymer having reactive groups along the length of the polymer, and the polymer is reacted with a limited molar quantity of a compound having the polymerizable group. For example, polysaccharides described herein have hydroxyl groups along the length of the polysaccharide, and a portion of these hydroxyl groups are reacted with a compound having a hydroxyl-reactive group and a polymerizable group.

In other cases one or more polymerizable groups are pendent from the macromer at one or more defined locations along the polymer backbone. For example, a polymer used for the synthesis of the macromer can have a reactive group at its terminus, or reactive groups at its termini. Many polymers prepared from monomers with reactive oxygen-containing groups (such as oxides) have hydroxyl-containing terminal ends which can be reacted with a compound having a hydroxyl-reactive group and a polymerizable group to provide the macromer with polymerizable groups at its termini.

The macromers are based on biocompatible polymers. The term "biocompatible" (which also can be referred to as "tissue compatible") generally refers to the inability of a component, composition, or article to promote a measurably adverse biological response in the body. A biocompatible component, composition, or article can have one or more of the following properties: non-toxic, non-mutagenic, non-allergenic, non-carcinogenic, and/or non-irritating. A biocompatible component, composition, or article, in the least, can be innocuous and tolerated by the body. A biocompatible component, by itself, may also improve one or more functions in the body.

EXAMPLES

Example 1

Preparation of a Disilane Degradable Linking Agent

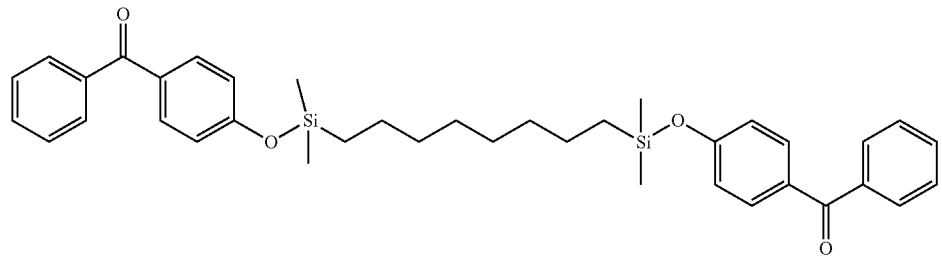 [SMILES: C[Si](C)(CCCCCCCC[Si](C)(C)Oc1ccc(C(=O)c2ccccc2)cc1)Oc1ccc(C(=O)c2ccccc2)cc1]

A degradable linking agent with the formula shown above can be prepared as follows:

4-hydroxybenzophenone (0.992 g) is placed in an oven-dried 50 mL round-bottom flask under inert atmosphere. Anhydrous DCM (30 mL) and pyridine (0.5 mL) is added to the reaction mixture. The reaction mixture is allowed to stir at room temperature for 5 min. 1,8-bis(chlorodimethylsilyl)octane (0.786 g) is added at once via syringe and the reaction mixture is allowed to stir for additional 16 h at room temperature. Product is purified by column chromatography using silica gel.

Example 2

Preparation of a Monosilane Degradable Linking Agent

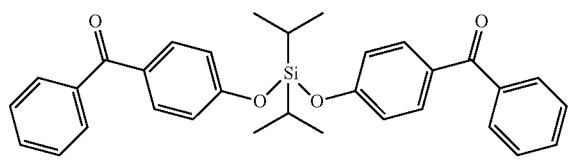 [SMILES: CC(C)[Si](Oc1ccc(C(=O)c2ccccc2)cc1)(Oc1ccc(C(=O)c2ccccc2)cc1)C(C)C]

A degradable linking agent with the formula shown above was prepared as follows:

4-hydroxybenzophenone (2 g) was placed in an oven-dried 100 mL round-bottom flask under inert atmosphere. Anhydrous DCM (50 mL) and pyridine (1.22 mL) was added to the reaction mixture. The reaction mixture is allowed to stir at room temperature for 5 min. Diisopropyldichlorosilane (1 g) was added at once via syringe and reaction mixture was allowed to stir for additional 16 h at room temperature. The reaction mixture was filtered and washed with DI water (2×25 mL), 0.5 N HCL (25 mL), DI water (25 mL), sat. aq. NaHCO$_3$ (25 mL) and DI water (25 mL). Solution was dried over Na$_2$SO$_4$ and solvent was evaporated in vacuo. Product was further purified by column chromatography using silica gel.

Example 3

Preparation of a Disilane Degradable Linking Agent

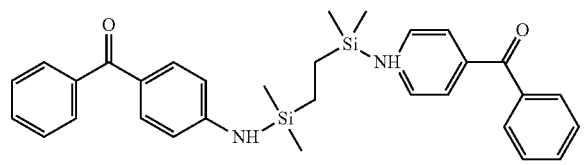

A degradable linking agent with the formula shown above can be prepared as follows:

4-aminobenzophenone (2 eq) is placed in an oven-dried round-bottom flask under inert atmosphere. Anhydrous DCM and pyridine (2.5 eq) is added to the reaction mixture. The reaction mixture is allowed to stir at room temperature for 5 min. 1,2-bis(chlorodimethylsilyl)methane (1 eq) is added at once via syringe and the reaction mixture is allowed to stir for additional 16 h at room temperature. Multifunctional structures are made by reacting more than 1 eq of 1,2-bis(chlorodimethylsilyl)methane with 4-aminobenzophenone to form a degradable linking agent having multiple photoreactive groups.

Example 4

Preparation of a Bis-phosphorous Degradable Linking Agent

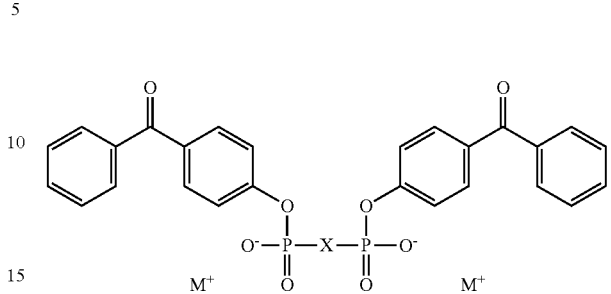

A degradable linking agent is formed by reacting methylenebis(phosphonic dichloride) (1 eq) with 4-hydroxybenzophenone (2 eq) in anhydrous DCM using pyridine (2.5 eq) as a base. The resulting product can be converted into its salt to increase water solubility.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The foregoing discloses embodiments of the invention. In the Specification and claims, the term "about" is used to modify, for example, the quantity of an ingredient in a composition, concentration, volume, process, and similar values and ranges thereof, to describe various embodiments of the disclosure. The term "about" refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. It should be readily apparent that any one or more of the design features described herein may be used in any combination with any particular configuration. With use of the metal injection molding process, such design features can be incorporated without substantial additional manufacturing costs. That the number of combinations are too numerous to describe, and the present invention is not limited by or to any particular illustrative combination described herein. The scope of the present subject matter should be determined with reference to the appended claims, along with the full scope of equivalents to which such claims are entitled.

What is claimed is:

1. A method of coating a support surface with a degradable linking agent in order to provide the support surface with one or more latent reactive groups, the method comprising:

a) providing the support surface;

b) applying to the support surface the degradable linking agent, wherein the degradable linking agent comprises a formula selected from:

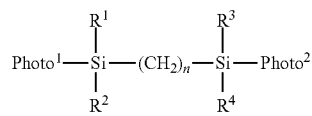

(i)

wherein $Photo^1$ and $Photo^2$, independently, represent a photoreactive group; n is an integer between 1 and 10; and $R^1$-$R^4$ are independently cyclic, linear or branched, saturated or unsaturated, aromatic or heteroaromatic, a photoreactive group, hydroxyl or salt thereof, or a combination thereof;

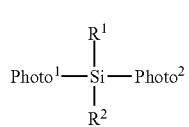

(ii)

wherein $Photo^1$ and $Photo^2$, independently, represent one or more photoreactive groups; and $R^1$ and $R^2$ are independently a photoreactive group, hydroxyl or salt thereof, or a combination thereof;

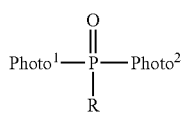

(iii)

wherein $Photo^1$ and $Photo^2$, independently, represent one or more photoreactive groups and R is hydroxyl or a salt thereof, or a combination thereof; and

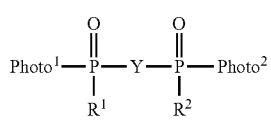

(iv)

wherein $Photo^1$ and $Photo^2$, independently, represent a photoreactive group, Y represents a linker that is null, an amine, an ether, linear or branched $C_1$-$C_{10}$ alkyl, or a combination thereof; and $R^1$ and $R^2$ are independently a photoreactive group, hydroxyl or salt thereof, cyclic, linear or branched hydrocarbon, saturated or unsaturated, aromatic or heteroaromatic, or a combination thereof; and c) illuminating the degradable linking agent upon the support surface under conditions suitable to activate a first photoreactive group to attach the degradable linking agent to the support surface, wherein a second photoreactive species remains unbound to the support surface and is able to revert to a latent reactive state.

2. A support surface bearing a coating comprising a polymer layer attached to the support surface by a degradable linking agent, wherein the degradable linking agent comprises a formula selected from:

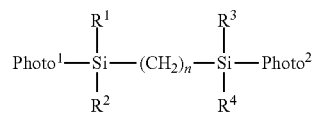

(i)

wherein $Photo^1$ and $Photo^2$, independently, represent a photoreactive group; n is an integer between 1 and 10; and $R^1$-$R^4$ are independently cyclic, linear or branched, saturated or unsaturated, aromatic or heteroaromatic, a photoreactive group, hydroxyl or salt thereof, or a combination thereof;

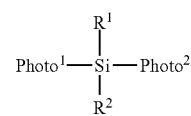

(ii)

wherein $Photo^1$ and $Photo^2$, independently, represent one or more photoreactive groups; and $R^1$ and $R^2$ are independently a photoreactive group, hydroxyl or salt thereof, or a combination thereof;

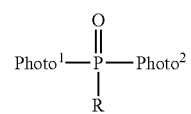

(iii)

wherein $Photo^1$ and $Photo^2$, independently, represent one or more photoreactive groups and R is hydroxyl or a salt thereof, or a combination thereof; and

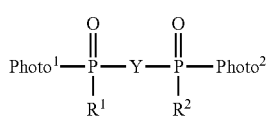

(iv)

wherein Photo¹ and Photo², independently, represent a photoreactive group, Y represents a linker that is null, an amine, an ether, linear or branched $C_1$-$C_{10}$ alkyl, or a combination thereof; and $R^1$ and $R^2$ are independently a photoreactive group, hydroxyl or salt thereof, cyclic, linear or branched hydrocarbon, saturated or unsaturated, aromatic or heteroaromatic, or a combination thereof; and wherein a first photoreactive group of the degradable linking agent, when activated in the presence of the support surface, is able to attach the degradable linking agent to the support surface, and a second photoreactive group of the degradable linking agent, when activated in the presence of a coating agent, is able to attach the coating to the support surface.

3. A coated medical device comprising: a medical device and a polymeric coating, wherein the coating is attached to the medical device by a degradable linking agent, wherein the degradable linking agent comprises a formula selected from:

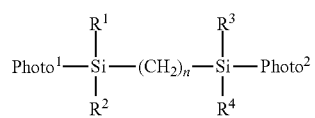

(i)

wherein Photo¹ and Photo², independently, represent a photoreactive group; n is an integer between 1 and 10; and $R^1$-$R^4$ are independently cyclic, linear or branched, saturated or unsaturated, aromatic or heteroaromatic, a photoreactive group, hydroxyl or salt thereof, or a combination thereof;

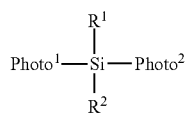

(ii)

wherein Photo¹ and Photo², independently, represent one or more photoreactive groups; and $R^1$ and $R^2$ are independently a photoreactive group, hydroxyl or salt thereof, or a combination thereof;

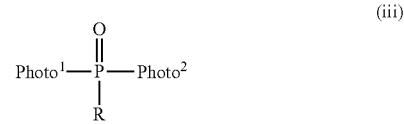

(iii)

wherein Photo¹ and Photo², independently, represent one or more photoreactive groups and R is hydroxyl or a salt thereof, or a combination thereof;

and

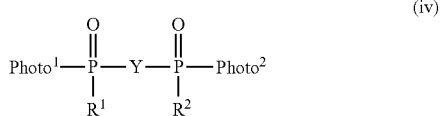

(iv)

wherein Photo¹ and Photo², independently, represent a photoreactive group, Y represents a linker that is null, an amine, an ether, linear or branched $C_1$-$C_{10}$ alkyl, or a combination thereof; and $R^1$ and $R^2$ are independently a photoreactive group, hydroxyl or salt thereof, cyclic, linear or branched hydrocarbon, saturated or unsaturated, aromatic or heteroaromatic, or a combination thereof.

4. The method of coating a support surface of claim 1, wherein the hydroxyl or salt thereof comprises a sodium salt, a potassium salt, a lithium salt, or a combination thereof.

5. The support surface of claim 2, wherein the hydroxyl or salt thereof comprises a sodium salt, a potassium salt, a lithium salt, or a combination thereof.

6. The coated medical device of claim 3, wherein the hydroxyl or salt thereof comprises a sodium salt, a potassium salt, a lithium salt, or a combination thereof.

7. The method of coating a support surface of claim 1, wherein one or more photoreactive groups comprise an aryl ketone.

8. The support surface of claim 2, wherein one or more photoreactive groups comprise an aryl ketone.

9. The coated medical device of claim 3, wherein one or more photoreactive groups comprise an aryl ketone.

10. The method of coating a support surface of claim 1, wherein one or more photoreactive groups comprise benzophenone.

11. The support surface of claim 2, wherein one or more photoreactive groups comprise benzophenone.

12. The coated medical device of claim 3, wherein one or more photoreactive groups comprise benzophenone.

* * * * *